Figure 4:
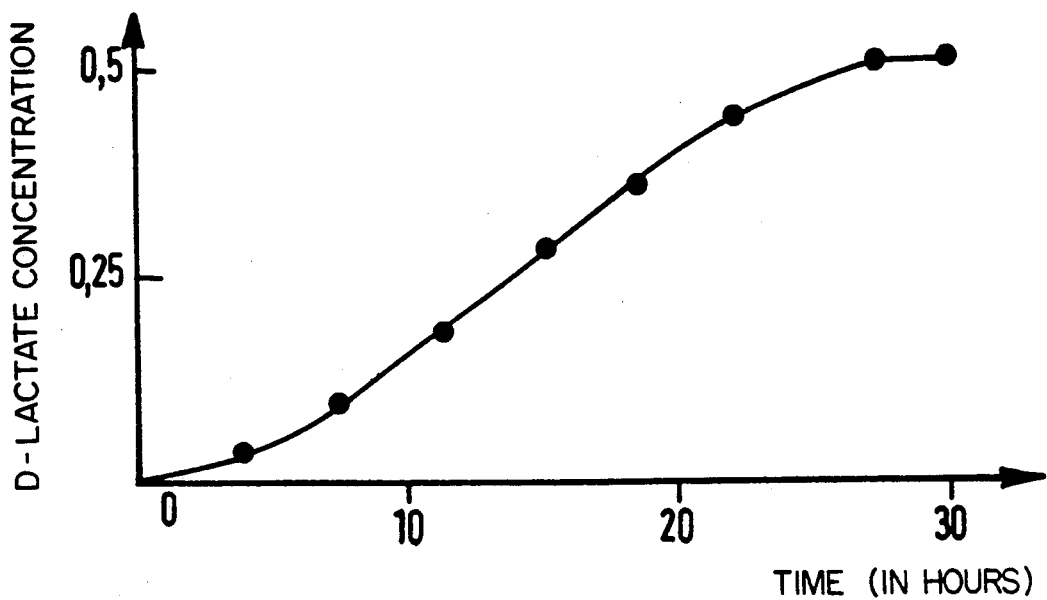

United States Patent [19]

Bourdillon et al.

[11] Patent Number: 5,192,687
[45] Date of Patent: Mar. 9, 1993

[54] ELECTROENZYMATIC METHOD FOR PRODUCING COMPOUNDS OF CONTROLLED ENANTIOMERIC PURITY

[75] Inventors: Christian Bourdillon, Le Meux; Jacques Moiroux; Jacques P. B. Bonnefoy, both of Paris; Jean-Marc Laval, Compiegne, all of France

[73] Assignee: Centre National de la Recherche Scientifique (CNRS), Paris, France

[21] Appl. No.: 432,760

[22] PCT Filed: Apr. 15, 1988

[86] PCT No.: PCT/FR88/00189

§ 371 Date: Sep. 29, 1989

§ 102(e) Date: Sep. 29, 1989

[87] PCT Pub. No.: WO88/08029

PCT Pub. Date: Oct. 20, 1988

[30] Foreign Application Priority Data

Apr. 17, 1987 [FR] France ............... 87 05547

[51] Int. Cl.$^5$ ............... C12P 7/02; C12P 13/04; C12P 7/56
[52] U.S. Cl. ............... 435/280; 435/106; 435/139
[58] Field of Search ............... 435/280, 106, 139

[56] References Cited

PUBLICATIONS

Maeda et al, Biotechnology and Bioengineering vol. XXVII: 596–602 (85).
Laane et al, Israel J. of Chem. 28:17–22 (1987/1988).
Sigma Catalog pp. 303, 601 (1985).
Bartalits et al, Clin. Chem. 30:1780–1783 (1984).
Bourdillon, "Biotechnology and Bioengineering", vol. 31, pp. 553–558, 1988.
Luisi, "TIBTECH", 153 to 161, Jun. 1986.
Laane, "Biotechnology and Bioengineering", vol. 30, pp. 81–87, 1987.
Biade, J.A.C.S., "Complete Conversion of L. Lactate into D-Lactate." (in publication).

Primary Examiner—Douglas W. Robinson
Assistant Examiner—S. Saucier
Attorney, Agent, or Firm—Jacobson, Price, Holman & Stern

[57] ABSTRACT

This process makes it possible to prepare a compound of controlled enantiomeric purity, D-P or L-P respectively, from a substrate S consisting of the oxidized form of the corresponding D/L-P racemate or of the said D/L-P racemate, or else of the optical isomer which is the inverse of that which it is wished to prepare. In accordance with this process, the said substrate S, the said D/L-P racemate or the optical isomer inverse of that which it is wished to prepare, respectively, is introduced into an electrochemical reactor together with an oxidoreductase enzyme capable of catalyzing the oxidation of the optical isomer which is the inverse of that which it is wished to prepare; a potential difference is applied between the electrodes in order to perform the nonstereospecific cathodic reduction of the said substrate S until the isomer having the required enantiomeric purity is obtained; and the cosubstrate of the said enzyme is regenerated by anodic oxidation in the said electrochemical reactor. The working examples are the production of D-lactate and D-malate.

18 Claims, 2 Drawing Sheets

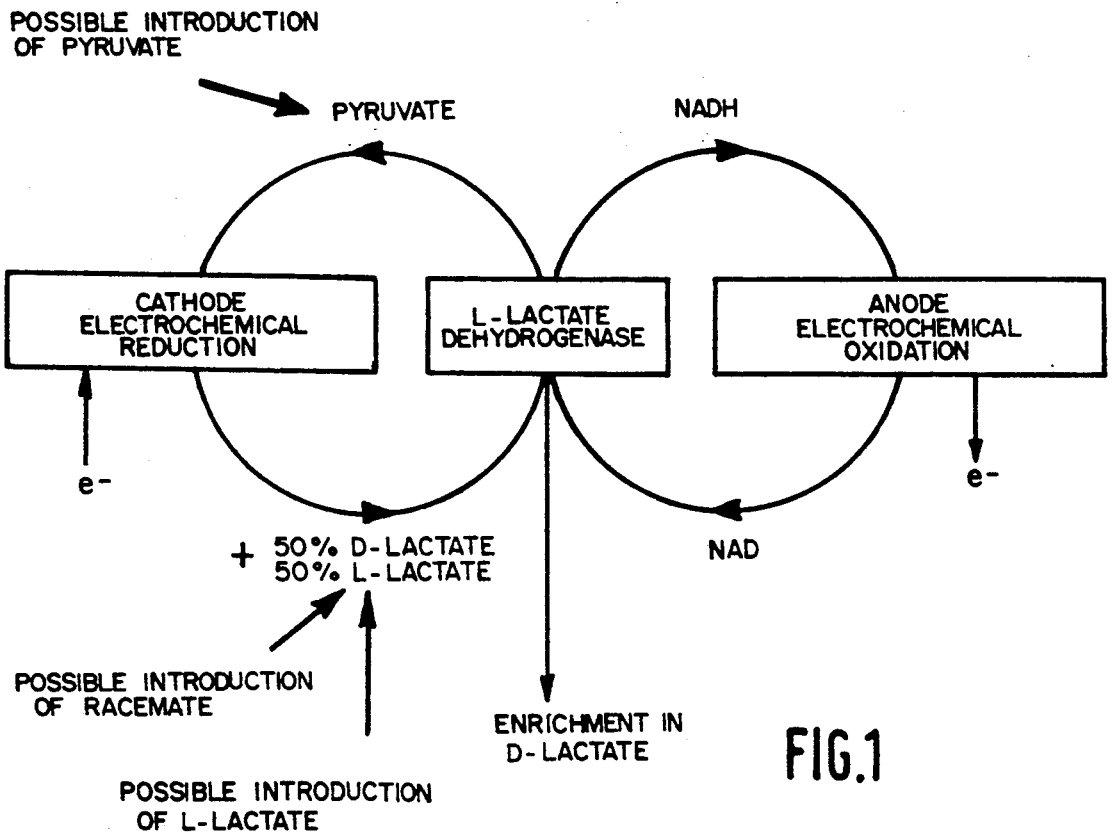
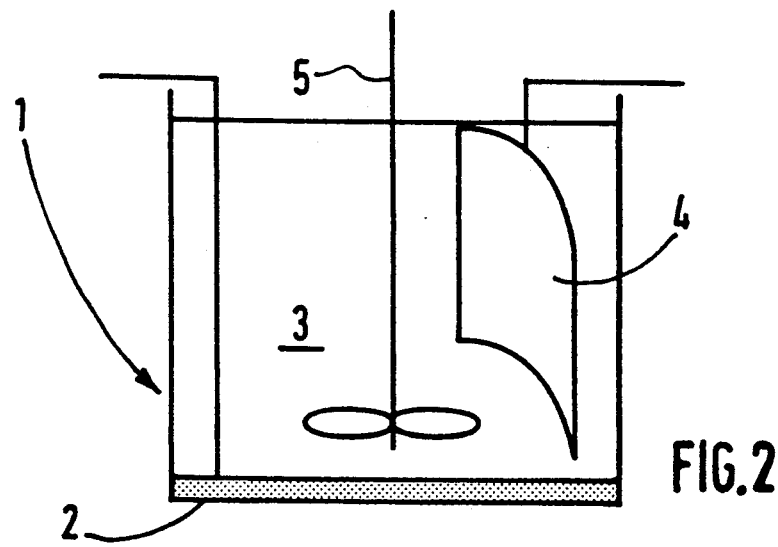

ELECTROENZYMATIC METHOD FOR PRODUCING COMPOUNDS OF CONTROLLED ENANTIOMERIC PURITY

The present invention relates, in a general way, to the use of reactions of oxidation and of reduction of organic molecules, in a process combining electrochemical reactions and enzyme catalysis and, in particular, an electroenzymatic process for producing a compound of controlled enantiomeric purity.

In living organisms electron exchanges are catalyzed by enzymes called oxidoreductases. These enzymes are of particular interest in enzyme technology, because they catalyze partial oxidation or reduction reactions. As an example of these enzymes there may be mentioned dehydrogenases and especially dehydrogenases with a cosubstrate of the type of nicotinamide adenine dinucleotide (denoted hereinafter by the abbreviation NAD) or nicotinamide adenine dinucleotide phosphate (denoted hereinafter by the abbreviation NADP), which are catalysts of high performance in their specificity and their selectivity. They catalyze reversible reactions of the type:

Reduced substrate +

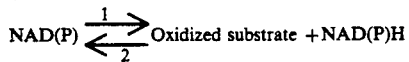

As a general rule the concerned substrates carry more or less oxygenated groups which are modified by the reaction.

The practical application of any process of the above-mentioned type assumes that it is possible to recycle the cosubstrate, namely, in the abovementioned example, the NAD(P) if it is desired to employ direction 1 of the above reaction, the result being an oxidation of the reduced substrate, or else the NAD(P)H, if it is desired to employ direction 2 of the above reaction, the result being a reduction of the oxidized substrate. In fact, NAD and NADP are molecules whose cost is such that it is necessary to be able to regenerate them cyclically several thousand times for the process to be economically acceptable.

Among the various methods of regeneration (chemical, enzymatic, microbiological and electrochemical), enzymatic regeneration, according to which a second enzyme, as well as other substrates, are employed to perform the regeneration, is currently considered to give the highest performance in respect of recycling capacity. However, it presents the disadvantage of complicating the process, in particular because it involves various separation stages. On the other hand, electrochemical regeneration is particularly attractive from this point of view, because no by-product is formed; however, electrochemical regeneration is still considered in the literature to give relatively poor performance.

Within the scope of the studies which have led to the present invention it was found that, contrary to this prejudice, electrochemical oxidation of NADH to NAD can be obtained with a very high yield (higher than 99.99%), and this makes it possible to obtain at least 10,000 regeneration cycles. Consequently the direct route for oxidizing a substrate (direction 1 of the above reaction scheme), employing dehydrogenases, can be applied industrially using the enzyme process.

On the other hand, direct electrochemical reduction of NAD to NADH leads to a very low number of regeneration cycles, fewer than 10, and, as a result, it is not possible to make use of this technique in an application performed on the industrial scale. Now, from the point of view of economy, it is precisely the reduction direction (direction 2 of the above reaction scheme) which is of interest, because it produces optically active compounds which are of a high purity and which are difficult to prepare by purely chemical methods.

By way of example there may be mentioned the chemical or electrochemical reduction of an unsymmetrical ketone, which produces a racemic mixture, difficult to purify, of D and L stereoisomers, as a general rule, in equimolar quantities.

As indicated above, the present invention is concerned with the production of these optically active compounds. In what follows, S will denote a starting substrate and P the end product, which carries an asymmetric carbon. P can be present in two optically active isomeric forms, written D-P and L-P, respectively. The (racemic) mixture of the two forms is written D/L-P.

The problem to be solved is that of obtaining, from S (or from D/L-P or else from the optical isomer which is the inverse of that which it is wished to prepare) reduced compounds L-P or D-P, of controlled enantiomeric purity, without the need to make use of electrochemical reduction of NAD or other cosubstrate of the oxidoreductase employed.

The solution provided by the present invention is based on the simultaneous use [1] of the nonstereospecific electrochemical reduction of the substrate S, resulting in the racemic D/L-P mixture, and [2] of the reverse oxidation which is catalyzed by the oxidoreductase enzyme and is stereospecific, resulting in the substrate S recycled in the nonstereospecific electrochemical reduction, the cosubstrate of the enzyme being advantageously regenerated by electrochemical oxidation. In these conditions, each cycle of S causes an enrichment in the isomer which has not been involved in the stereospecific oxidation.

The reaction scheme of the two main reactions [1] and [2], which are partially antagonistic, and of the electrochemical oxidation of the cosubstrate of the enzyme employed, in the case where the latter is L-dehydrogenase whose cosubstrate is NAD, is the following:

In this case, since the D-P isomer is not converted, each cycle of S causes an enrichment in D-P. In the same way, by choosing a D-dehydrogenase, the system can be enriched in the L-P isomer.

The subject of the present invention is therefore, first of all, an electroenzymatic process for producing a compound of controlled enantiomeric purity, D-P or L-P respectively, from a substrate S consisting of the oxidized form of the corresponding D/L-P racemate, or of the said D/L-P racemate, or else from the optical isomer inverse of that which it is intended to prepare, characterized in that the said substrate S, the said D/L-P racemate or the optical isomer inverse of that which it is wished to prepare, respectively, is introduced into an electrochemical reactor together with an oxidoreductase enzyme capable of catalyzing the oxidation of the optical isomer which is the inverse of that which it is wished to prepare; in that a potential difference is applied between the electrodes in order to perform the nonstereospecific cathodic reduction of the said substrate S until the isomer having the required enantiomeric purity is obtained; and in that the cosubstrate of the said enzyme is regenerated by anodic oxidation in the said electrochemical reactor.

This process applies especially to the production of optically active compounds denoted by the general formulae:

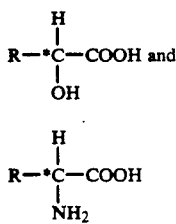

When it is desired to obtain a compound of formula (I), the corresponding α-ketocarboxylic acid (or a salt of this acid) is introduced as substrate S, and when it is desired to obtain a compound of formula (II), the corresponding α-ketocarboxylic acid (or a salt of this acid) is introduced as substrate S in the presence of aqueous ammonia, the reductions resulting in the α-alcohol-acid of formula (I) or in the α-aminoacid of formula (II) taking place according to the following reaction schemes:

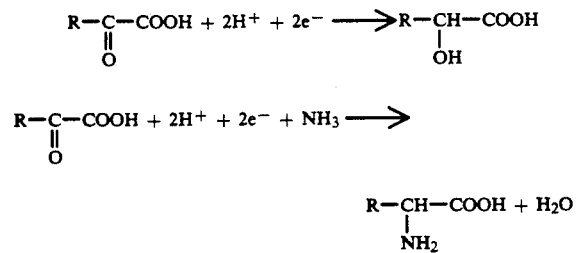

By way of examples of compounds which can be prepared according to the present invention there may be mentioned lactic acid, malic acid, which are compounds of formula (I)—and their salts—, and many α-aminoacids, such as α-alanine, which are compounds of formula (II).

The list of the compounds which can be prepared is not exhaustive, the only condition being that it should be possible to associate the two antagonistic reactions which are at the basis of the invention, namely the nonstereospecific electrochemical reduction and the stereospecific enzymatic oxidation, according to the following criteria:

availability, or possibility of induction in a living organism, of the specific enzyme of the P isomer inverse of that which it is desired to prepare; and feasibility of the electrochemical reduction of S in physicochemical conditions which are compatible with the functioning of the enzyme.

As enzyme, it is possible to introduce a dehydrogenase with a natural cosubstrate, such as NAD or NADP, or else an oxidase, with an artificial cosubstrate (that is to say not normally involved in metabolic chains), chosen especially from electron acceptors, such as quinones, ferrocene, ferricyanide and dyes, for example dichlorophenolindophenol.

D- or L-lactate dehydrogenases, L-malate dehydrogenase, L-alanine dehydrogenase and D- or L-aminoacid oxidases may be mentioned by way of particular examples.

According to the invention, the reaction is advantageously conducted in a solvent medium, especially in water or in an organic solvent compatible with maintaining the enzyme activity, while permitting the supply of protons during the reduction, water being preferred. Water-organic solvent mixtures can also be employed.

The enzyme may be in solution in the reaction medium or else may be immobilized on nonporous or porous particles, such as the foams described in the paper by G. Broun, D. Thomas, G. Gellf, D. Domurado, A. M. Berjonneau and C. Guillon, Biotechnology and Bioengineering 15, 359-375 (1973), these particles being immersed in the reaction medium, or else the enzyme may be immobilized on the anode, advantageously as described in C. Bourdillon, J. P. Bourgeois and D. Thomas, Journal of American Chemical Society, Vol 102, 1st page 4231 (1980).

In the case where the enzyme employed is a dehydrogenase with an NAD or NADP cosubstrate, the pH of the medium may be between 6 and 10 (which corresponds to the maximum stability region for the cosubstrate NAD(H) and NADP(H); the working potential of the anode, between 0.5 and 0.9 V/electrode containing calomel and saturated KCl (SCE); and the working potential of the cathode between −0.7 and −1.5 V/SCE.

The working potential of the anode is chosen so that only NADH is oxidized. In general this does not present any problem because the OH or NH₂ groups of the products are oxidizable only starting from 1.5 V/SCE.

The choice of the cathode working potential is presented in the same terms. The interfering reduction of NADH begins from −0.9 V/SCE according to the following reaction:

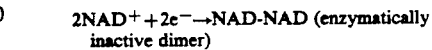
2NAD⁺ +2e⁻→NAD-NAD (enzymatically inactive dimer)

The working potential is chosen so that the rate of reduction of S should be higher than that of the NAD dimerization. The formation of the dimer can, nevertheless, be tolerated, because it is easily reoxidized to an enzymatically active monomer at the anode at about 0.2 V/SCE. This increases the energy consumption, but allows the substrates to be reduced, if necessary, at potentials below −0.9 V/SCE.

In the case where the enzyme employed is an oxidase whose cosubstrate is an electron acceptor, the pH of the reaction medium may be between 4 and 8; the working potential of the anode between 0.1 and 0.9 V/SCE; and the working potential of the cathode between −0.7 and −1.5 V/SCE.

Furthermore, according to the invention, it is possible to employ a cathode made of a material chosen from metals, for example mercury and nickel, and carbon, and an anode made of a material chosen from carbon and metals, for example noble metals, such as platinum-coated titanium. The electrodes may assume various shapes.

FIG. 1 of the attached drawing shows the reaction scheme summarizing the process in the case of the use of an L-lactate dehydrogenase as enzyme and of pyruvate as substrate.

The three possible routes for employing the process are shown in this diagram, namely that apart from the introduction of S and the complete conversion to D-P, it is also possible either to introduce the L/D-P racemate and to perform the resolution of this racemate to L-P, or else to introduce the isomer L-P and to perform an inversion of its configuration.

The overall result corresponds to the disappearance of S and/or of L-P. Only electrical energy and catalytic quantities of NAD and of enzyme are consumed.

FIG. 2 shows diagrammatically a first electrochemical reactor 1 in which the process of the invention can be used in an extremely simple way. This reactor 1 comprises a single compartment, on the bottom of which lies a layer of mercury 2, employed as cathode. The compartment is filled with a solution 3 containing an acid/base buffer serving as electrolyte, the enzyme and the substrate to be converted. An anode 4 made of carbon (or of platinum-coated titanium), and a stirrer 5 are immersed in the solution 3.

The process is conducted noncontinuously by applying a potential difference between the two electrodes 2 and 4 until the substrate is completely converted.

Figure 3:
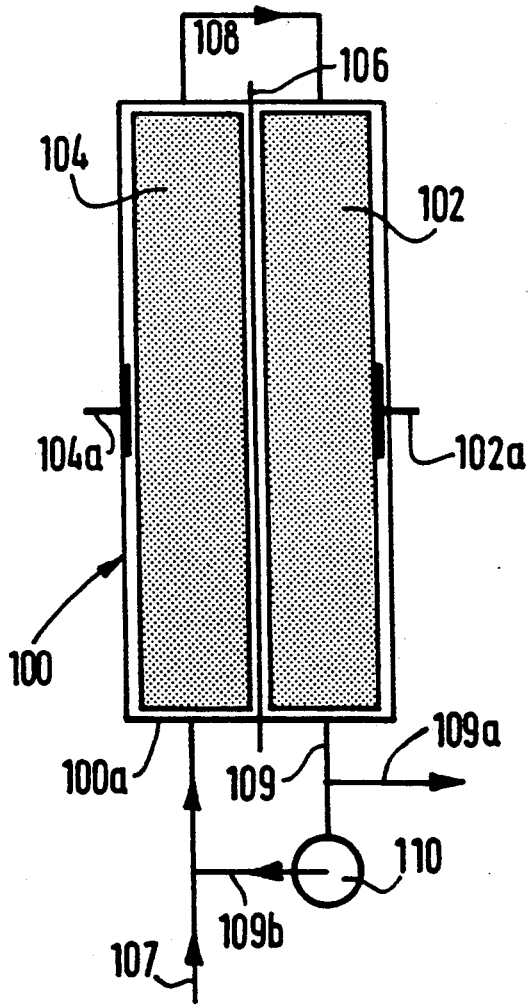

FIG. 3 shows diagrammatically a second reactor 100, with a recycle loop, which can also be employed for making use of the process of the invention.

This reactor 100 comprises an enclosure 100a containing a cathode 102, made of carbon felt, and an anode 104, also made of carbon felt ("RVG 4000", marketed by the "Carbone Lorraine" company), on which the enzyme employed is immobilized (according to the procedure indicated hereinafter), the cathode and anode being separated by an ion exchange membrane 106 acting as a separator between the two compartments.

Each electrode is connected to a current-collector, 102a and 104a respectively.

The solution to be treated enters the anode compartment via the line 107 and is extracted from this compartment via the line 108 and, from there, it is returned to the cathode compartment 102, from which it is extracted via the line 109, which includes a first branch 109a which is the product exit line and a branch 109b, which is a branch for recycling into the entry line 107, a recirculation pump 110 being situated in the path of this branch 109b.

Two examples of use of the process according to the present invention will be given in what follows.

EXAMPLE 1

Production of D-lactate from pyruvate

The reaction scheme is the following:

$$2H^+ + \text{pyruvate} + 2e^- \xrightarrow{\text{cathode}}$$

racemic mixture of D- and L-lactate

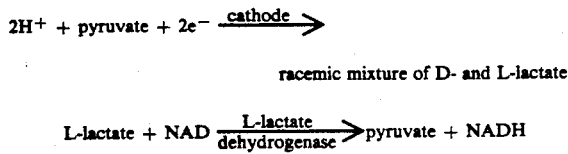

$$NADH \xrightarrow{\text{anode}} NAD^+ + H^+ + 2e^-$$

Concentrated pyruvate (3M) is introduced at a rate of 0.6 cm³/h into a reactor of the type of that shown in FIG. 2, containing 100 cm³ of pH 8, 0.5M phosphate buffer, 2 mg of L-lactate dehydrogenase (E.C.1.1.1.27.) (type 2 from the "Sigma" company) and 7 mg of NAD.

In parallel, the potential difference between the anode and the cathode is progressively raised to 1.8 volts in the space of ¼ hour. With the stationary state of the reactor being established in approximately 1 hour, the pyruvate feed and the potential difference are maintained so that the pyruvate concentration is always at $10^{-3}$M, to limit the reverse reaction of the dehydrogenase. The reaction is continued for 30 hours and the current decreases slowly from 240 to 140 mA. Introduction of the pyruvate is stopped one hour before stopping the reactor.

FIG. 4 shows the change in the concentration of D-lactate in the reactor, as a function of time. The concentration reaches 45 g/l of D-lactate when the reactor is stopped, including less than 1% of residual L-lactate and pyruvate.

The conversion of one mole of pyruvate to D-lactate consumes 4×F coulombs in the abovementioned experimental conditions (reactor fed).

EXAMPLE 2

Production of D-lactate from racemic D+L-lactate

The procedure is as shown in Example 1, racemic lactate being introduced instead of the pyruvate. The same concentration of D-lactate as in Example 1 is obtained in the space of 19 hours with currents of the order of 160 mA. As previously, the NAD was regenerated approximately 10,000 times.

The conversion of one mole of racemate consumes 2×F coulombs in the abovementioned experimental conditions.

EXAMPLE 3

Continuous production of D-malate from the racemic mixture D+L-malate

The reaction scheme is the following:

$$\text{L-malate} + NAD \xrightarrow[\text{dehydrogenase}]{\text{L-malate}} \text{oxaloacetate} + NADH$$

$$\text{oxaloacetate} + 2H^+ + 2e^- \xrightarrow{\text{cathode}} D + \text{L-malate racemate}$$

$$NADH \xrightarrow{\text{anode}} NAD + 2e^- + 2H^+$$

This process is used with a percolating solution reactor of the type of that shown in FIG. 3. The immobilization of the enzyme is performed by direct grafting of the protein onto the electrode for regenerating NAD (anode). This configuration is particularly advantageous for ensuring the shift of the thermodynamic equilibrium, which does not favor the formation of oxaloacetate.

Method of immobilization of the enzyme (according to the abovementioned technique):

The carbon (graphite) felt constituting the anode is first of all oxidized superficially by chemical treatment in concentrated $HNO_3$ at 105° C. It is then mounted in the reactor and then rinsed by circulating water until the pH is neutral. 40 cm³ of the immobilization solution are introduced into the felt by circulation and are then left to stand for 12 hours in order that the polymerization may be complete. The immobilization solution contains 10 mg of L-malate dehydrogenase (E.C.1.1.1.37.) (manufactured by the "Sigma" company)+ 10 mg of 1-cyclohexyl-3-(2-morpholinoethyl)-carbodiimide methoxy-p-toluenesulfonate (manufactured by the "Sigma" company) in 40 cm³ of pH 7.5, 0.02M phosphate buffer.

After rinsing for 1 hour using the working buffer (0.5M, pH 8.5 phosphate buffer) the reactor is ready for use.

The operation of the reactor in a stationary regime corresponds to the following parameters:

the volume of the working buffer circulating in the reactor loop is 100 cm³;

the throughput of the recycling pump 110 is 0.5 l/h;

the racemic mixture containing 1 mole per liter of malate and $10^{-4}$ mole per liter of NAD in the working buffer is introduced via the line 107 at a rate of 5 cm³/h;

the potential difference between the anode and the cathode is maintained at 1.7V and the resulting current is approximately 0.3 ampere;

the concentration of the species in the reactor in the stationary state are $10^{-2}$M for the sum of oxaloacetate +L-malate, $10^{-4}$ for NAD+NADH, and 1M for D-malate.

These concentrations are those obtained in the exit line 109a. The D-malate is pure to within 1% in this experiment. This purity can be increased or reduced by adjusting the throughput of the recycling pump 110.

We claim:

1. A process for producing a compound of controlled enantiomeric purity, D-isomer or L-isomer, respectively, from a) a substrate which consists of the oxidized form of the corresponding D/L-P racemate, b) the D/L-P racemate, or c) the optical isomer which is the inverse of that desired; the process comprising introducing (a), (b), or (c), together with an oxidoreductase enzyme capable of catalyzing reversible oxidation of (c) to form a reaction medium, into an electrochemical reactor having electrodes, applying sufficient potential difference between the electrodes to effect non-stereospecific cathodic reduction of (a) until the compound having the desired enantiomeric purity is obtained, and regenerating cosubstrate of the enzyme by anodic oxidation in the electrochemical reactor.

2. An electroenzymatic process according to claim 1, wherein the substrate S is an α-ketocarboxylic acid or an α-ketocarboxylic acid in the presence of aqueous ammonia.

3. An electroenzymatic process according to claim 1, wherein the D/L-P racemate is an α-alcohol acid or an α-amino acid.

4. An electroenzymatic process according to claim 1, wherein the enzyme is a dehydrogenase or an oxidase.

5. An electroenzymatic process according to claim 4, wherein the enzyme is a dehydrogenase having a natural cosubstrate.

6. An electroenzymatic process according to claim 4, wherein the enzyme is an oxidase having a cosubstrate selected from the group consisting of a quinone, ferrocene, ferricyanide and electron-acceptor dye.

7. An electroenzymatic process according to claim 1, which comprises conducting the reaction in a solvent medium, in which the solvent is compatible with maintaining enzyme activity.

8. An electroenzymatic process according to claim 1, which is conducted in a reaction medium in which the enzyme is in solution.

9. An electroenzymatic process according to claim 1, which is conducted in a reaction medium in which the enzyme, immobilized on porous or nonporous particles, is immersed.

10. An electroenzymatic process according to claim 1, wherein the enzyme is immobilized on the anode.

11. An electroenzymatic process according to claim 1, according to which the enzyme employed is a dehydrogenase whose substrate is NAD or NADP, wherein the pH of the reaction medium is between 6 and 10; the working potential of the anode, between 0.5 and 0.9 V/electrode containing calomel and saturated KCl (SCE) and the working potential of the cathode between −0.7 and −1.5 V/SCE.

12. An electroenzymatic process according to claim 1, according to which the enzyme employed is an oxidase whose cosubstrate is an electron acceptor, and wherein the pH of the reaction medium is situated between 4 and 8; the working potential of the anode, between 0.1 and 0.9 V/SCE; and the working potential of the cathode, between −0.7 and −1.5 V/SCE.

13. An electroenzymatic process according to claim 1, wherein the electrochemical reactor has a cathode made of a material selected from the group consisting of metal and carbon and an anode made of a material selected from the group consisting of carbon and metal.

14. A process according to claim 5 wherein the neutral cosubstrate is a member selected from the group consisting of nicotinamide adenine dinucleotide and nicotinamide adenine dinucleotide phosphate.

15. A process according to claim 1 wherein the enzyme is in solution in the reaction medium or is immobilized on porous or nonporous particles immersed in the reaction medium.

16. A process according to claim 15 wherein the reduction is effected in a solvent medium wherein the solvent is compatible with maintaining enzyme activity while permitting a supply of protons during the reduction.

17. A process according to claim 16 wherein the enzyme is a dehydrogenase whose cosubstrate is NAD or NADP, the pH of the reaction medium is between 6 and 10, one of the electrodes is an anode having a working potential between 0.5 and 0.9 V/electrode containing calomel and saturated KCl (SCE), and one of the electrodes is a cathode having a working potential between −0.7 and −0.5 V/SCE.

18. A process according to claim 17 wherein the cathode is a metal or carbon cathode, and the anode is a carbon metal anode.

* * * * *